US000001829H

United States Statutory Invention Registration [19]

[11] Reg. Number: H1,829

Bereznak

[45] Published: Jan. 4, 2000

[54] FUNGICIDAL FUSED BICYCLIC PYRIMIDINONES

[75] Inventor: James Francis Bereznak, Aston, Pa.

[73] Assignee: E. I. du Pont de Nemours and Company, Wilmington, Del.

[21] Appl. No.: 08/333,179

[22] Filed: Nov. 2, 1994

[51] Int. Cl.[7] ..... C07D 239/72

[52] U.S. Cl. ..... 544/285; 514/259

[58] Field of Search ..... 544/285; 514/259

[56] References Cited

U.S. PATENT DOCUMENTS 3,755,582 8/1973 Bullock ..... 424/251
3,867,384 2/1975 Bullock et al. ..... 260/256.4

FOREIGN PATENT DOCUMENTS

WO 94/26722 11/1994 WIPO ..... C07D 239/95

*Primary Examiner*—Peter A. Nelson

[57] ABSTRACT

This invention pertains to compounds of Formula I including all geometric and stereoisomers, N-oxides, agriculturally-suitable salts thereof, agricultural compositions containing them and their use as fungicides:

I

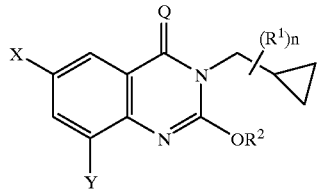

wherein:

Q is O or S; and n, $R^1$, $R^2$, X, and Y are described in the text.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FUNGICIDAL FUSED BICYCLIC PYRIMIDINONES

This invention relates to certain 4(3H)-quinazolinones, their agriculturally suitable salts and compositions, and methods of their use as general or selective fungicides, in particular for the control of cereal powdery mildew both preventive and curative.

U.S. Pat. Nos. 3,755,582 and 3,867,384 disclose certain 4(3H)-quinazolinone fungicides. These patents, however, do not specifically disclose the compounds of the present invention.

SUMMARY OF THE INVENTION

This invention comprises compounds of Formula I including all geometric and stereoisomers, N-oxides, agriculturally-suitable salts thereof, agricultural compositions containing them and their use as fungicides:

I

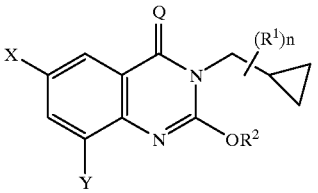

wherein:

n is 0–4;

Q is O or S;

each $R^1$ is independently selected from the group $C_1$–$C_4$ alkyl, $C_1$–$C_2$ haloalkyl and halogen;

$R^2$ is selected from the group $C_3$–$C_{10}$ alkyl, $C_5$–$C_7$ cycloalkyl, $C_3$–$C_{10}$ alkenyl, $C_3$–$C_{10}$ alkynyl, $C_4$–$C_{10}$ cycloalkylalkyl and $C_2$–$C_{10}$ alkoxyalkyl;

X is halogen;

Y is hydrogen or halogen;

provided that (i) when n is 1 and $R^1$ is $C_1$–$C_4$ alkyl or n is 2 and both $R^1$ are $C_1$–$C_4$ alkyl, then at least one $R^1$ is attached to the cyclopropyl ring; and (ii) when n is 0, Q is O, $R^2$ is n-propyl, and Y is H, then X is F, Cl or I.

DETAILED DESCRIPTION OF THE INVENTION

Terms are used in the above recitations in accordance with the following denotations.

"Alkyl", used either alone or in compound words such as "haloalkyl" denotes straight-chain or branched alkyl; e.g., methyl, ethyl, n-propyl, i-propyl, or the different butyl, pentyl, hexyl, etc. isomers.

"Cycloalkyl" denotes cyclopropyl, cyclobutyl, cyclopentyl, cyclohexyl, and cycloheptyl.

"Cycloalkylalkyl" denotes a cycloalkyl ring attached to a branched or straight-chain alkyl; e.g., cyclopropylmethyl and cyclohexylbutyl.

"Alkenyl" denotes straight chain or branched alkenes; e.g., 1-propenyl, 2-propenyl, 3-propenyl and the different butenyl , pentenyl, hexenyl, etc. isomers. "Alkenyl" also denotes polyenes such as 1,3-hexadiene and 2,4,6-heptatriene.

"Alkynyl" denotes straight chain or branched alkynes; e.g., ethynyl, 1-propynyl, 3-propynyl and the different butynyl, pentynyl, hexynyl, etc. isomers. "Alkynyl" can also denote moieties comprised of multiple triple bonds; e.g., 2,7-octadiyne and 2,5,8-decatriyne.

"Alkoxy" denotes methoxy, ethoxy, n-propyloxy, isopropyloxy and the different butoxy, pentoxy, hexyloxy, etc. isomers.

The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CF_2$.

The total number of carbon atoms in a substituent group is indicated by the "$C_i$–$C_j$" prefix where i and j are numbers from 1 to 10. For example, $C_1$–$C_3$ alkoxyl designates methoxy through propyloxy; $C_2$ alkoxyalkyl designates $CH_3OCH_2$; $C_3$ alkoxyalkyl designates, for example, $CH_3OCH_2CH_2$ or $CH_3CH_2OCH_2$; and $C_4$ alkoxyalkyl designates the various isomers of an alkoxy group substituted with a second alkyl group containing a total of 4 carbon atoms, examples including $CH_3CH_2CH_2OCH_2$ and $CH_3CH_2OCH_2CH_2$.

Preferred for reasons of ease of synthesis or greater fungicidal activity are:

Preferred 1. The compounds of Formula I as defined above, or agriculturally-suitable salts thereof, wherein:

Q is O;

$R^1$ is selected from the group $C_1$–$C_2$ alkyl, $C_1$–$C_2$ haloalkyl and halogen; and $R^2$ is selected from the group $C_3$–$C_5$ alkyl, $C_5$ cycloalkyl, $C_3$–$C_5$ alkenyl, $C_3$–$C_5$ alkynyl, $C_4$–$C_6$ cycloalkylalkyl and $C_2$–$C_5$ alkoxyalkyl.

Preferred 2. The compounds of Preferred 1 wherein:

$R^1$ is selected from the group $CH_3$, $CF_3$ and halogen; and $R^2$ is selected from the group $C_3$–$C_5$ alkyl, $C_3$–$C_5$ alkenyl, $C_3$–$C_5$ alkynyl and $C_2$–$C_5$ alkoxyalkyl.

Preferred 3. The compounds of Preferred 2 wherein:

X is Cl, Br, or I.

Preferred 4. The compounds of Preferred 3 wherein:

$R^2$ is selected from the group $C_3$–$C_5$ alkyl, $C_3$–$C_5$ alkenyl and $C_3$–$C_5$ alkynyl.

Preferred 5. The compounds of Preferred 4 wherein said compounds are selected from the group:

3-(cyclopropylmethyl)-6-iodo-2-propyloxy-4(3H)-quinazolinone, 3-(cyclopropylmethyl)-6,8-diiodo-2-propyloxy-4(3H)-quinazolinone, 3-(cyclopropylmethyl)-6,8-dibromo-2-propyloxy-4(3H)-quinazolinone and 6-chloro-3-(cyclopropylmethyl)-2-propyloxy-4(3H)-quinazolinone.

It is recognized that some reagents and reaction conditions described below for preparing compounds of Formula I may not be compatible with some functionalities claimed for $R^1$, $R^2$, n, Q, X, and Y. In these cases, the incorporation of protection/deprotection sequences into the synthesis may be necessary in order to obtain the desired products. The cases in which protecting groups are necessary, and which protecting group to use, will be apparent to one skilled in chemical synthesis. See Greene, T. W. and Wuts, P. G. M.; *Protective Groups in Organic Synthesis,* 2nd Ed.; John Wiley & Sons, Inc.; New York, (1980) for suitable protecting groups.

In the following description of the preparation of compounds of Formula I, compounds of Formulae I*a* (Formula I where Q is 0) and l*b* (Formula I where Q is S) are various subsets of the compounds of Formula I. All substituents in compounds of Formulae Ia and Ib and 2–5 are as defined above for Formula I.

Compounds of this invention can exist as one or more stereoisomers. The various stereoisomers include enantiomers, diastereomers and geometric isomers. One skilled in the art will appreciate that one stereoisomer may be more active than the others and how to separate said stereoisomers. Accordingly, the present invention comprises mixtures, individual stereoisomers, and optically active mixtures of compounds of Formula I, as well as agriculturally suitable salts thereof.

The compounds of Formula I can be prepared as described below in Schemes 1–3 and in the Example.

Synthesis of Compounds of Formula I

Compounds of Formula Ia, compounds of Formula I wherein Q is O, can be made by the method illustrated in Scheme 1.

An anthranilic acid (2-aminobenzoic acid) of Formula 2 is condensed with an isothiocyanate of Formula 1 to form the 2-thioquinazolinedione of Formula 3. This condensation is preferably performed in the presence of a base such as triethylamine. S-Methylation of this compound affords the 2-methylthio-4(3H)-quinazolinone of Formula 4.

For the introduction of the $R^2O$ group, the 2-methylthio-4(3H)-quinazolinone of Formula 4 is treated with a mixture of a base, for example sodium hydride, in $R^2OH$ solvent. The reaction mixture is stirred at a temperature from about 0° C. to 120° C. for 1–120 hours. The desired 2-$R^2O$-4(3H)-quinazolinone can be isolated from the reaction mixture by extraction into a water-immiscible solvent, and purified by chromatography or recrystallization. Similar synthetic procedures are described in U.S. Pat. No. 3,755,582, incorporated herein by reference.

Scheme 1

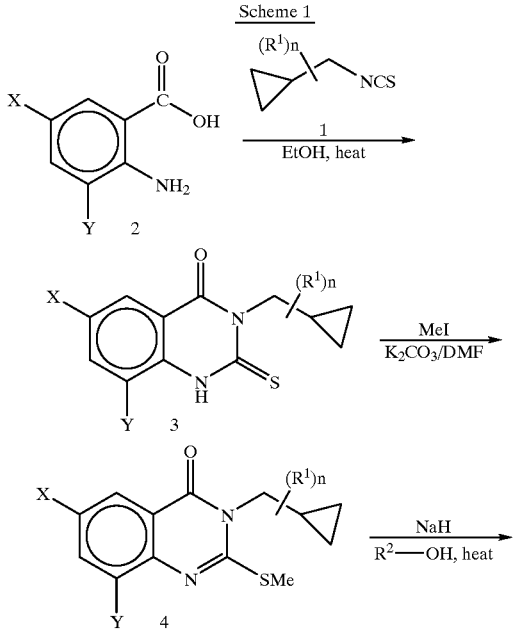

-continued

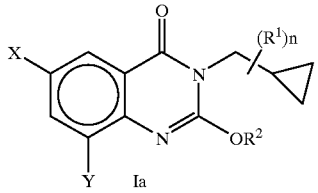

Anthranilic acids of Formula 2 are known or can be prepared by known methods. For example see, March, J. *Advanced Organic Chemistry;* 3rd ed., John Wiley: New York, (1985), p 983. The isothiocyanates of Formula 1 can be prepared from the corresponding amine by treatment with thiophosgene as known in the art. For example, see *J. Heterocycl. Chem.,* (1990), 27, 407.

Alternatively, 2-thioquinazolinediones of Formula 3 can be prepared by treatment of the ($C_1$–$C_4$ alkyl) anthranilic acid ester of Formula 5 with thiophosgene to form the isothiocyanate ester, followed by treatment with an amine of Formula 6 (Scheme 2).

Scheme 2

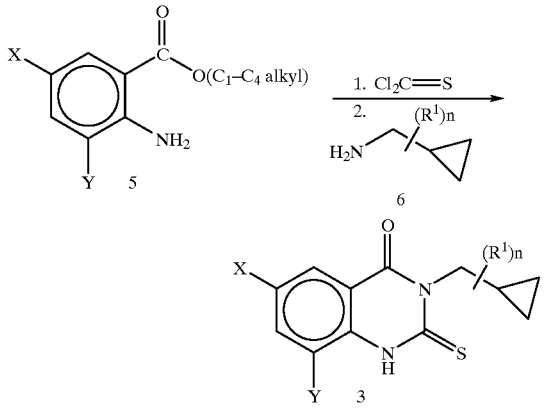

The anthranilic acid ester of Formula 5 is treated with thiophosgene at a temperature from about −20° C. to 100° C. for 1 to 48 hours optionally in an inert solvent. Often this reaction is performed in a biphasic mixture in the presence of a base, such as calcium carbonate, and an acid, such as aqueous hydrochloric acid. The resulting isothiocyanate may be isolated by extraction into a water-immiscible solvent, such as methylene chloride, followed by drying of the organic extracts and evaporation under reduced pressure. Alternatively, the isothiocyanate can be combined in situ with the amine of Formula 6 and stirred at about −20° C. to 50° C. for 0.1 to 24 hours. The desired 2-thioquinazolinediones of Formula 3 can be isolated from the reaction mixture by aqueous extraction, and purified by chromatography or recrystallization. Similar synthetic procedures are described in *J. Heterocycl. Chem.,* (1990), 27, 407.

Compounds of Formula Ib, compounds of Formula I wherein Q is S, can be prepared as illustrated in Scheme 3.

Scheme 3

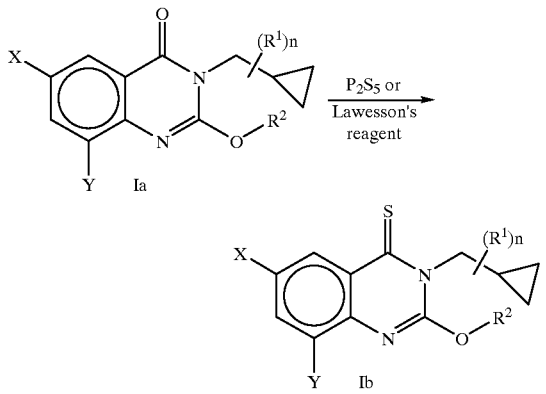

Treatment of the quinazolinone of Formula Ia with phosphorous pentasulfide or Lawesson's reagent [2,4-bis(4-methoxyphenyl)-1,3-dithia-2,4-diphosphetane-2,4-disulfide] in an inert solvent such as dioxane at a temperature from 0° C. to the reflux temperature of the solvent for 0.1 to 72 hours affords the quinazolinethione of Formula Ib. This procedure is described in the literature, for example see U.S. Pat. No. 3,755,582.

In addition to the methods described above, compounds of Formula Ia can be prepared by displacement of the 2-chlorine in the appropriate 4(3H)-quinazolinone, rather than by displacement of the 2-$SCH_3$ group (Scheme 1). The appropriate 2-chlorine compounds for this method can be prepared as described in U.S. Pat. No. 3,867,384.

Salts of compounds of Formula I can be formed by treating the free base of the corresponding compound with strong acids such as hydrochloric or sulfuric acid. N-Oxides of compounds of Formula I can be made by oxidizing the corresponding reduced nitrogen compound with a strong oxidizing agent such as meta-chloroperoxybenzoic acid.

EXAMPLE

Synthesis of 3-(Cyclopropylmethyl)-6-iodo-2-propyloxy-4(3H)-quinazolinone

Step A:

A mixture of 2-amino-5-iodo-benzoic acid (6.2 g), triethylamine (2.4 g) and cyclopropylmethyl isothiocyanate (2.5 g) in ethanol (35 mL) is heated under reflux for 18 h. After cooling to 0° C., the reaction mixture is filtered and the filter cake is washed with ethanol and hexanes to deliver 6.3 g of intermediate A.

Step B:

Iodomethane (5.0 mL) is added to the product of Step A (5.7 g) and potassium carbonate (22.17 g) in dimethylformamide (160 mL) at room temperature. After stirring at room temperature for 3 h, the reaction mixture is concentrated to dryness in vacuo and the resulting residue is partitioned between 450 mL each of ethyl acetate and water. Following separation of the organic layer and additional washings with water and brine (250 mL each), the organic layer is dried ($Na_2SO_4$ anhydrous), and concentrated in vacuo. The resulting residue is treated with cold hexanes and filtered to provide Intermediate B.

Step C:

A solution of sodium propoxide in DMF (prepared by adding 0.50 g of 60% NaH/mineral oil to a solution of 0.73 g n-propanol in 15 mL DMF) is treated with the product of Step B (1.2 g) and stirred at room temperature for 1 h. The reaction is then quenched with 1 mL aqueous $NaHCO_3$ and concentrated to dryness in vacuo. The residue so obtained is partitioned between $CH_2CI_2$ and water (200 rnL each) and the organic phase is separated. After washing with more water and brine, the $CH_2Cl_2$ phase is dried ($Na_2SO_4$ anhydrous), concentrated, and purified by column chromatography to afford the title compound.

Using the procedures outlined in Schemes 1–3 and the above Example, the compounds of Tables 1–9 hereinafter can be prepared. The formula referred to in the Tables which follow is illustrated below:

I

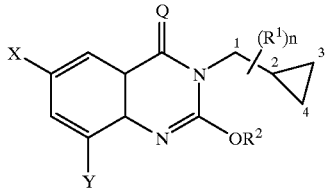

The following abbreviations are used in the Tables which follow. All alkyl groups are the nornal isomers unless indicated otherwise.

| | |
|---|---|
| t = tertiary | Et = ethyl |
| n = normal | Pr = propyl |
| i = iso | c = cyclo |
| Me = methyl | Bu = butyl |

TABLE 1

Compounds of Formula I wherein Q = O, X = I, Y = H, $R^2$ = n-propyl and

| $(R^1)_n$ | $(R^1)_n$ | $(R^1)_n$ | $(R^1)_n$ | $(R^1)_n$ |
|---|---|---|---|---|
| H | 3-$CF_3$ | 3,3,4,4-tetra-F | 3-Me | 3,3-di-$CF_2CF_3$ |
| 2-Et | 1-Me, 3-$CF_3$ | 1-Et, 3-i-Pr, 4,4-di-F | 3-n-Bu | 3-$CCl_2CF_3$ |
| 3,3-di-F | 3,3-di-Me | 3,3-di-Cl | 3,4-di-Et | 3,3-di-Br |
| 3,4-di-Cl | 3-t-Bu | 3,3-di-Et, 4,4-di-Cl | 1-Me, 3-Pr | 2-Me, 3-i-Bu |

TABLE 2

Compounds of Formula I wherein Q = O, X = I, Y = H, $(R^1)_n$ = H and

| $R^2$ | $R^2$ | $R^2$ |
|---|---|---|
| n-Bu | c-pentyl | —$(CH_2)_4$-c-hexyl |
| n-decyl | —$CH_2C{\equiv}CH$ | —$CH_2OCH_3$ |
| —$CH_2CH{=}CH_2$ | —$(CH_2)_3C{\equiv}CH$ | —$(CH_2)_5O(CH_2)_4CH_3$ |
| —$CH_2$-(c-propyl) | —$CH_2CH(CH_3)CH{=}CH_2$ | —$(CH_2)_7$-(c-propyl) |
| c-heptyl | —$(CH_2)_5C{\equiv}C(CH_2)_2CH_3$ | —$CH(Et)C{\equiv}C$—Et |
| n-hexyl | —$CH_2CH_2CH(CH_3)_2$ | —$(CH_2)_2CH{=}CHCH_3$ |
| —$CH_2$-(c-pentyl) | —$(CH_2)_2OCH_2CH_3$ | —$(CH_2)_8CH{=}CH_2$ |

TABLE 3

Compounds of Formula I wherein $(R^1)_n$ = H, $R^2$ = n-propyl and

| Q | X | Y | Q | X | Y |
|---|---|---|---|---|---|
| O | Cl | H | S | Cl | H |
| O | F | H | S | Br | H |
| O | Cl | Cl | S | Cl | Cl |

TABLE 3-continued

| Compounds of Formula I wherein $(R^1)_n$ = H, $R^2$ = n-propyl and | | | | | |
|---|---|---|---|---|---|
| Q | X | Y | Q | X | Y |
| O | F | F | S | F | F |
| O | I | Cl | S | I | H |
| O | Br | Br | S | I | I |
| O | I | Br | S | Br | Br |
| O | Br | I | S | I | Br |

TABLE 4

| Compounds of Formula I wherein W = O, X = I, Y = I, $(R^1)_n$ = H and | | |
|---|---|---|
| $R^2$ | $R^2$ | $R^2$ |
| n-Bu | c-pentyl | —$(CH_2)_4$-c-hexyl |
| n-decyl | —$CH_2C{\equiv}CH$ | —$CH_2OCH_3$ |
| —$CH_2CH{=}CH_2$ | —$(CH_2)_3C{\equiv}CH$ | —$(CH_2)_5O(CH_2)_4CH_3$ |
| —$CH_2$-(c-propyl) | —$CH_2CH(CH_3)CH{=}CH_2$ | —$(CH_2)_7$-(c-propyl) |
| c-heptyl | —$(CH_2)_5C{\equiv}(CH_2)_2CH_3$ | —CH(Et)C≡C—Et |
| n-hexyl | —$CH_2CH_2CH(CH_3)_2$ | —$(CH_2)_2CH{=}CHCH_3$ |
| —$CH_2$-(c-pentyl) | —$(CH_2)_2OCH_2CH_3$ | —$(CH_2)_8CH{=}CH_2$ |

TABLE 5

| Compounds of Formula I wherein Q = O, X = I, Y = I, $R^2$ = n-propyl and | | | | |
|---|---|---|---|---|
| $(R^1)_n$ | $(R^1)_n$ | $(R^1)_n$ | $(R^1)_n$ | $(R^1)_n$ |
| H | 3-$CF_3$ | 3,3,4,4-tetra-F | 3-Me | 3,3-di-$CF_2CF_3$ |
| 2-Et | 1-Me, 3-$CF_3$ | 1-Et, 3-i-Pr, 4,4-di-F | 3-n-Bu | 3-$CCl_2CF_3$ |
| 3,3-di-F | 3,3-di-Me | 3,3-di-Cl | 3,4-di-Et | 3,3-di-Br |
| 3,4-di-Cl | 3-t-Bu | 3,3-di-Et, 4,4-di-Cl | 1-Me, 3-Pr | 2-Me, 3-i-Bu |

TABLE 6

| Compounds of Formula I wherein Q = O, X = Br, Y = H, $R^2$ n-propyl and | | | | |
|---|---|---|---|---|
| $(R^1)_n$ | $(R^1)_n$ | $(R^1)_n$ | $(R^1)_n$ | $(R^1)_n$ |
| 1,1-di-F | 3-$CF_3$ | 3,3,4,4-tetra-F | 3-Me | 3,3-di-$CF_2CF_3$ |
| 2-Et | 1-Me, 3-$CF_3$ | 1-Et, 3-i-Pr, 4,4-di-F | 3-n-Bu | 3-$CCl_2CF_3$ |
| 3,3-di-F | 3,3-di-Me | 3,3-di-Cl | 3,4-di-Et | 3,3-di-Br |
| 3,4-di-Cl | 3-t-Bu | 3,3-di-Et, 4,4-di-Cl | 1-Me, 3-Pr | 2-Me, 3-i-Bu |

TABLE 7

| Compounds of Formula I wherein Q = O, X = Br, Y = H, $(R^1)_n$ = H and | | |
|---|---|---|
| $R^2$ | $R^2$ | $R^2$ |
| n-Bu | c-pentyl | —$(CH_2)_4$-c-hexyl |
| n-decyl | —$CH_2C{\equiv}CH$ | —$CH_2OCH_3$ |
| —$CH_2CH{=}CH_2$ | —$(CH_2)_3C{\equiv}CH$ | —$(CH_2)_5O(CH_2)_4CH_3$ |
| —$CH_2$-(c-propyl) | —$CH_2CH(CH_3)CH{=}CH_2$ | —$(CH_2)_7$-(c-propyl) |
| c-heptyl | —$(CH_2)_5C{\equiv}C(CH_2)_2CH_3$ | —CH(Et)C≡C—Et |
| n-hexyl | —$CH_2CH_2CH(CH_3)_2$ | —$(CH_2)_2CH{=}CHCH_3$ |
| —$CH_2$-(c-pentyl) | —$(CH_2)_2OCH_2CH_3$ | —$(CH_2)_8CH{=}CH_2$ |

TABLE 8

| Compounds of Formula I wherein Q = O, X = Br, Y = Br, $(R^1)_n$ = H and | | |
|---|---|---|
| $R^2$ | $R^2$ | $R^2$ |
| n-Bu | c-pentyl | —$(CH_2)_4$-c-hexyl |
| n-decyl | —$CH_2C{\equiv}CH$ | —$CH_2OCH_3$ |
| —$CH_2CH{=}CH_2$ | —$(CH_2)_3C{\equiv}CH$ | —$(CH_2)_5O(CH_2)_4CH_3$ |
| —$CH_2$-(c-propyl) | —$CH_2CH(CH_3)CH{=}CH_2$ | —$(CH_2)_7$-(c-propyl) |
| c-heptyl | —$(CH_2)_5C{\equiv}C(CH_2)_2CH_3$ | —CH(Et)C≡C—Et |
| n-hexyl | —$CH_2CH_2CH(CH_3)_2$ | —$(CH_2)_2CH{=}CHCH_3$ |
| —$CH_2$-(c-pentyl) | —$(CH_2)_2OCH_2CH_3$ | —$(CH_2)_8CH{=}CH_2$ |

TABLE 9

| Compounds of Formula I wherein Q = O, X = Br, Y = Br, $R^2$ n-propyl and | | | | |
|---|---|---|---|---|
| $(R^1)_n$ | $(R^1)_n$ | $(R^1)_n$ | $(R^1)_n$ | $(R^1)_n$ |
| 1,1-di-F | 3-$CF_3$ | 3,3,4,4-tetra-F | 3-Me | 3,3-di-$CF_2CF_3$ |
| 2-Et | 1-Me, 3-$CF_3$ | 1-Et, 3-i-Pr, 4,4-di-F | 3-n-Bu | 3-$CCl_2CF_3$ |
| 3,3-di-F | 3,3-di-Me | 3,3-di-Cl | 3,4-di-Et | 3,3-di-Br |
| 3,4-di-Cl | 3-t-Bu | 3,3-di-Et, 4,4-di-Cl | 1-Me, 3-Pr | 2-Me, 3-i-Bu |

Formulation/Utility

Compounds of this invention will generally be used in formulation with an agriculturally suitable composition. The fungicidal compositions of the present invention 10 comprise an effective amount of at least one compound of Formula I as defined above and at least one of (a) a surfactant, (b) an organic solvent, and (c) at least one solid or liquid diluent. Useful formulations can be prepared in conventional ways. They include dusts, granules, pellets, solutions, suspensions, emulsions, wettable powders, emulsifiable concentrates, dry flowables and the like. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents and solvents are described in Marsden, *Solvents Guide,* 2nd Ed., Interscience, New York, (1950). *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, (1964), list surfactants and recommended uses. All formulations can contain minor amounts of additives to reduce foam, caking, corrosion, microbiological growth, and the like.

Methods for formulating such compositions are well known. Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations,* Washington, D.C., (1988), pp 251 . 259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering,* Dec. 4, 1967, pp 147–148, *Perry's Chemical Engineer's Handbook,* 4th Ed., McGraw-Hill, New York, (1963), pp 8–57 and following, and WO 91/13546. Pellets can be prepared as described in U.S. Pat. No. 4,172,714. Water-dispersible and water-soluble granules can be prepared as taught in DE 3,246,493.

For further information regarding the art of formulation, see U.S. Pat. No. 3,235,361, Col. 6, line 16 through Col. 7, line 19 and Examples 10 through 41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, (1961), pp 81–96; and Hance et al., *Weed Control Handbook,* 8th Ed., Blackwell Scientific Publications, Oxford, (1989).

In the following Examples, all percentages are by weight and all formulations are prepared in conventional ways.

EXAMPLE A

| Wettable Powder | |
|---|---|
| 3-(Cyclopropylmethyl)-6-iodo-2-propyloxy-4(3H)-quinazolinone | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE B

| Granule | |
|---|---|
| 3-(Cyclopropylmethyl)-6-iodo-2-propyloxy-4(3H)-quinazolinone | 10.0% |
| attapulgite granules (low volative matter, 0.71/0.30 mm; U.S.S. No. 25–50 sieves) | 90.0% |

EXAMPLE C

| Extruded Pellet | |
|---|---|
| 3-(Cyclopropylmethyl)-6-iodo-2-propyloxy-4(3H)-quinazolinone | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE D

| Emulsifiable Concentrate | |
|---|---|
| 3-(Cyclopropylmethyl)-6-iodo-2-propyloxy-4(3H)-quinazolinone | 20.0% |
| blend of oil soluble sulfonates and polyoxyethylene ethers | 10.0% |
| isophorone | 70.0% |

The compounds of this invention are useful as plant disease control agents, especially for the control of cereal powdery mildews (e.g., *Erysiphe graminis* f sp. tritici, the causal agent of wheat powdery mildew). The present invention therefore further comprises a method for controlling plant diseases caused by fungal plant pathogens comprising applying to the plant or portion thereof to be protected, or to the plant seed or seedling to be protected, an effective amount of a compound of Formula I (or an N-oxide or agriculturally-suitable salt thereof) or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidewnatum, Alternaria brassicae, Septoria nodorum, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerothecafuliginea, Fusarium oxysporum, Verticillium dahliae, Pythium aphanidennatum, Phytophthora megasperma* and other generea and species closely related to these pathogens.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as acephate, avermectin B, azinphosmethyl, bifenthrin, biphenate, buprofezin, carbofuran, chlordimeform, chlorpyrifos, cyfluthrin, deltamethrin, diazinon, diflubenzuron, dimethoate, esfenvalerate, fenpropathrin, fenvalerate, fipronil, flucythrinate, flufenprox, fluvalinate, fonophos, isofenphos, malathion, metaldehyde, methamidophos, methidathion, methomyl, methoprene, methoxychlor, monocrotophos, oxamyl, parathion-methyl, permethrin, phorate, phosalone, phosmet, phosphamidon, pirimicarb, profenofos, rotenone, sulprofos, terbufos, tetrachlorvinphos, thiodicarb, tralomethrin, trichlorfon and triflumuron; fungicides such as benomyl, blasticidin S, bromuconazole, captafol, captan, carbendazim, chloroneb, chlorothalonil, copper oxychloride, copper salts, cymoxanil, cyproconazole, cyrodinil, dichloran, diclobutrazol, diclomezine, difenoconazole, diniconazole, dodine, edifenphos, epoxyconazole fenarimol, fenbuconazole, fenpropidine, fenpropimorph, fluquinconazole, flusilazol, flutolanil, flutriafol, folpet, furalaxyl, hexaconazole, ipconazole, iprobenfos, iprodione, isoprothiolane, kasugamycin, mancozeb, maneb, mepronil, metalaxyl, metconazole, myclobutanil, neo-asozin, oxadixyl, penconazole, pencycuron, phosethyl-Al, probenazole, prochloraz, propiconazole, pyrifenox, pyrimethanil, pyroquilon, sulfur, tebuconazole, tetraconazole, thiabendazole, thiophanate-methyl, thiuram, triadimefon, triadimenol, tricyclazole, triticonazole, uniconzole, validamycin and vinclozolin; nematocides such as aldoxycarb, fenamiphos and fosthietan; bactericides such as oxytetracyline, streptomycin and tribasic copper sulfate; acaricides such as amitraz, binapacryl, chlorobenzilate, cyhexatin, dicofol, dienochlor, fenbutatin oxide, hexythiazox, oxythioquinox, propargite and tebufenpyrad; and biological agents such as Bacillus thuringiensis and baculovirus.

In certain instances, combinations with other fungicides having a similar spectrum of control but a different mode of action will be particularly advantageous for resistance management. Preferred combinations comprise a compound of Formula I and a fungicide selected from the group flusilazole, cyproconazole, tetraconazole, fenpropimorph, fenpropidine, cymoxanil, benomyl, carbendazim, mancozeb, and maneb.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

The following TEST demonstrates the control efficacy of compounds of this invention on wheat powdery mildew. The pathogen control protection afforded by the compounds is not limited, however, to this pathogen.

Test compounds are first dissolved in acetone in an amount equal to 3% of the final volume and are then suspended at a concentration of 200 ppm in purified water containing 250 ppm of the surfactant Trem® 014 (polyhydric alcohol esters). The resulting test suspensions are then used in the following test.

TEST

The test suspension is sprayed to the point of run-off on wheat seedlings. The following day the seedlings are inoculated with a spore dust of *Erysiphe graminis* f. sp. tritici, (the causal agent of wheat powdery mildew) and incubated in a growth chamber at 20° C. for 7 days, after which disease ratings are made.

Control of wheat powdery mildew is observed in this test.

I claim:

1. A compound of Formula I

I

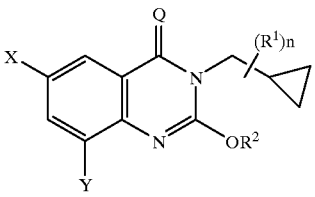

or an N-oxide or agriculturally-suitable salt thereof; wherein:

n is 0–4;

Q is O or S;

$R^1$ is independently selected from the group $C_1$–$C_4$ alkyl, $C_1$–$C_2$ haloalkyl and halogen;

$R^2$ is selected from the group $C_3$–$C_{10}$ alkyl, $C_5$–$C_7$ cycloalkyl, $C_3$–$C_{10}$ alkenyl, $C_3$–$C_{10}$ alkynyl, $C_4$–$C_{10}$ cycloalkylalkyl and $C_2$–$C_{10}$ alkoxyalkyl;

X is halogen;

Y is hydrogen or halogen;

provided that (i) when n is 1 and $R^1$ is $C_1$–$C_4$ alkyl or n is 2 and both $R^1$ are $C_1$–$C_4$ alkyl, then at least one $R^1$ is attached to the cyclopropyl ring; and (ii) when n is 0, Q is O $R^2$ is n-propyl, and Y is H, then X is F, Cl or I.

2. A compound of claim 1 having said Formula I, or an agriculturally-suitable salt thereof; wherein:

Q is O;

$R^1$ is selected from the group $C_1$–$C_2$ alkyl, $C_1$–$C_2$ haloalkyl and halogen; and $R^2$ is selected from the group $C_3$–$C_5$ alkyl, $C_5$ cycloalkyl, $C_3$–$C_5$ alkenyl, $C_3$–$C_5$ alkynyl, $C_4$–$C_6$ cycloalkylalkyl and $C_2$–$C_5$ alkoxyalkyl.

3. A compound of claim 2 wherein:

$R^1$ is selected from the group $CH_3$, $CF_3$ and halogen; and $R^2$ is selected from the group $C_3$–$C_5$ alkyl, $C_3$–$C_5$ alkenyl, $C_3$–$C_5$ alkynyl and $C_2$–$C_5$ alkoxyalkyl.

4. A compound of claim 3 wherein:

X is Cl, Br, or I.

5. A compound of claim 4 wherein:

$R^2$ is selected from the group $C_3$–$C_5$ alkyl, $C_3$–$C_5$ alkenyl and $C_3$–$C_5$ alkynyl.

6. A compound of claim 5 which is selected from the group:

3-(cyclopropylmethyl)-6-iodo-2-propyloxy-4(3H)-quinazolinone, 3-(cyclopropylmethyl)-6,8-diiodo-2-propyloxy-4(3H)-quinazolinone 3-(cyclopropylmethyl)-6,8-dibromo-2-propyloxy-4(3H)-quinazolinone and 6-chloro-3-(cyclopropylmethyl)-2-propyloxy-4(3H)-quinazolinone.

7. A method for controlling plant diseases caused by fungal plant pathogens comprising applying to the plant or portion thereof to be protected, to the media in which the plant to be protected is growing, or to the plant seed or seedling to be protected an effective amount of a compound of Formula I:

I

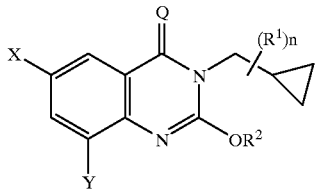

or an N-oxide or agriculturally-suitable salt thereof; wherein:

n is 0–4;

Q is O or S;

$R^1$ is independently selected from the group $C_1$–$C_4$ alkyl, $C_1$–$C_2$ haloalkyl and halogen;

$R^2$ is selected from the group $C_3$–$C_{10}$ alkyl, $C_5$–$C_7$ cycloalkyl, $C_3$–$C_{10}$ alkenyl, $C_3$–$C_{10}$ alkynyl, $C_4$–$C_{10}$ cycloalkylalkyl and $C_2$–$C_{10}$ alkoxyalkyl;

X is halogen;

Y is hydrogen or halogen;

provided that (i) when n is 1 and $R^1$ is $C_1$–$C_4$ alkyl or n is 2 and both $R^1$ are $C_1$–$C_4$ alky, then at least one $R^1$ is attached to the cyclopropyl ring; and (ii) when n is 0, Q is O, $R^2$ is n-propyl, and Y is H, then X is F, Cl or I.

8. A fungicidal composition comprising an effective amount of a compound of Formula I:

I

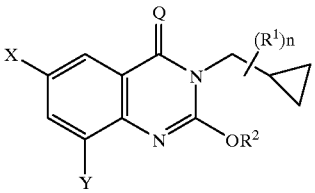

or an N-oxide or agriculturally-suitable salt thereof; wherein:

n is 0–4;

Q is O or S;

$R^1$ is independently selected from the group $C_1$–$C_4$ alkyl, $C_1$–$C_2$ haloalkyl and halogen;

$R^2$ is selected from the group $C_3$–$C_{10}$ alkyl, $C_5$–$C_7$ cycloalkyl, $C_3$–$C_{10}$ alkenyl, $C_3$–$C_{10}$ alkynyl, $C_4$–$C_{10}$ cycloalkylalkyl and $C_2$–$C_{10}$ alkoxyalkyl;

X is halogen;

Y is hydrogen or halogen;

provided that (i) when n is 1 and $R^1$ is $C_1$–$C_4$ alkyl or n is 2 and both $R^1$ are $C_1$–$C_4$ alkyl, then at least one $R^1$ is attached to the cyclopropyl ring; and (ii) when n is 0, Q is O, $R^2$ is n-propyl, and Y is H, then X is F, Cl or I; and at least one of (a) a surfactant, (b) an organic solvent, and (c) at least one solid or liquid diluent.

9. A method for controlling wheat powdery mildew comprising applying to the plant or portion thereof to be protected, to the media in which the plant to be protected is growing, or to the plant seed or seedling to be protected an effective amount of a compound of claim 1.

* * * * *